United States Patent [19]

De Jong et al.

[11] Patent Number: 4,857,497

[45] Date of Patent: Aug. 15, 1989

[54] SUPPORTED METAL CATALYSTS AND USE THEREOF

[75] Inventors: Krijn P. De Jong; Johannes H. E. Glezer; Martin F. M. Post, all of Amsterdam, Netherlands

[73] Assignee: Shell Oil Company, Houston, Tex.

[21] Appl. No.: 186,782

[22] Filed: Apr. 25, 1988

Related U.S. Application Data

[63] Continuation of Ser. No. 924,004, Oct. 28, 1986, abandoned.

[30] Foreign Application Priority Data

Nov. 8, 1985 [GB] United Kingdom ................ 8527549

[51] Int. Cl.$^4$ .................. B01J 21/06; B01J 21/08; B01J 23/74
[52] U.S. Cl. .................... 502/242; 502/258; 502/261; 585/408; 585/419; 585/640; 585/700; 518/713; 518/715; 518/721
[58] Field of Search .............. 502/242, 258, 261; 518/713, 715, 721; 585/408, 418, 319, 322, 640, 310, 419, 700

[56] References Cited

U.S. PATENT DOCUMENTS

| | | | |
|---|---|---|---|
| 3,067,127 | 12/1962 | Plank et al. | 502/242 |
| 3,159,569 | 12/1964 | Hansford | 502/242 |
| 3,300,414 | 1/1964 | Meyer-Simon et al. | 502/242 |
| 3,457,192 | 7/1969 | Housset et al. | 502/242 |
| 3,930,812 | 1/1976 | Harris et al. | 48/197 |
| 3,988,262 | 10/1976 | Andersen et al. | 252/466 |
| 4,002,658 | 1/1977 | Betta et al. | 260/448 |
| 4,240,933 | 12/1980 | Copelin | 502/242 |
| 4,284,531 | 8/1981 | Simpson et al. | 502/242 |
| 4,385,193 | 5/1983 | Bijwaard et al. | 502/242 |
| 4,459,372 | 7/1984 | Arena | 502/242 |
| 4,499,209 | 2/1985 | Hoek et al. | 502/242 |
| 4,518,703 | 5/1985 | Young | 502/242 |
| 4,521,531 | 6/1985 | Coates | 502/242 |
| 4,522,939 | 6/1985 | Minderhoud et al. | 502/242 |
| 4,576,968 | 3/1986 | Nay et al. | 518/713 |
| 4,581,343 | 4/1986 | Blanchard et al. | 502/242 |
| 4,594,468 | 6/1986 | Minderhoud | 502/242 |
| 4,599,481 | 7/1986 | Post et al. | 585/700 |
| 4,637,993 | 1/1987 | van Erp et al. | 502/242 |

FOREIGN PATENT DOCUMENTS

| | | | |
|---|---|---|---|
| 0009802 | 4/1980 | European Pat. Off. | 502/242 |
| 9802 | 4/1980 | European Pat. Off. | |
| 30110 | 10/1981 | European Pat. Off. | |
| 0152553 | 11/1980 | Japan | 502/242 |
| 55-152553 | 11/1980 | Japan | |
| 58-153538 | 9/1983 | Japan | |
| 0153538 | 9/1983 | Japan | 502/242 |
| 58-189036 | 11/1983 | Japan | |
| 195461 | 6/1983 | New Zealand | 518/715 |
| 196076 | 6/1983 | New Zealand | 518/715 |
| 210202 | 3/1984 | New Zealand | 518/715 |
| 2104405 | 3/1983 | United Kingdom | 502/242 |
| 2130113 | 5/1984 | United Kingdom | 502/242 |

*Primary Examiner*—H. M. S. Sneed
*Assistant Examiner*—Helane Myers
*Attorney, Agent, or Firm*—Y. Grace Tsang

[57] ABSTRACT

A catalyst comprising a silica-containing carrier on which a metal component iron, nickel, or cobalt promoted by zirconium is supported snd, in addition, as promoter a noble metal from Group VIII of the Periodic Table; the promoter cobalt/zirconium catalyst is suitable for the preparation of hydrocarbons from carbon monoxide and hydrogen.

10 Claims, No Drawings

4,857,497

SUPPORTED METAL CATALYSTS AND USE THEREOF

This is a continuation of application Ser. No. 924,004, filed Oct. 28, 1986 now abandoned.

FIELD OF THE INVENTION

The invention relates to catalyst systems comprising a silica containing carrier on which a metal selected from the group consisting of iron, cobalt and nickel is supported. In particular, the invention relates to a supported metal catalyst suitable for the preparation of hydrocarbons from carbon monoxide and hydrogen.

BACKGROUND OF THE INVENTION

The preparation of hydrocarbons from a $H_2/CO$ mixture by contacting this mixture with a catalyst at elevated temperatures and pressures is known in the literature as the Fischer-Tropsch synthesis.

Catalysts often used for this purpose comprise one or more metals from the iron group supported on a carrier.

A very active catalyst system consists of cobalt supported on a silica carrier and, as promoter, zirconium.

The Fischer-Tropsch catalysts are suitably prepared by combining the active ingredients and the carrier, e.g. by precipitating the metal on the carrier from an aqueous solution of the metal or, preferably, by impregnating the carrier material with a compound of the metal in the presence of a liquid. Moreover, kneading techniques may be applied, especially if it is intended to prepare catalysts to be used in slurry reactors. In all preparation procedures, the liquid is removed from the composition followed by calcination and reduction.

In the calcination step, the impregnated metal compound is converted into one or more metal oxides. In order to be catalytically active in the conversion of carbon monoxide and hydrogen, it is necessary that a substantial amount of the metal oxide(s) be reduced under formation of the metal. The reduction is carried out in the presence of hydrogen usually at elevated temperatures, e.g. in the range of 200°-300° C. It has been observed that in some cases in the compositions to be used as catalysts, metal hydrosilicates occur, which do not exhibit catalytic activity. Because the reduction of these hydrosilicates is laborious, or requires severe conditions, it has been investigated whether the formation of the said hydrosilicates can be minimized, or that their removal can be facilitated.

It has now been found that by incorporating a specific further metal promoter in the catalyst the reduction step is considerably facilitated.

SUMMARY OF THE INVENTION

The invention relates to a catalyst system comprising a silica containing carrier on which as metal component iron, nickel, or cobalt promoted by zirconium is supported whereby the system in addition contains as promoter a noble metal from Group VIII of the Periodic Table.

The invention relates in particular to a catalyst suitable for the preparation of hydrocarbons from carbon monoxide and hydrogen, which catalyst comprises cobalt supported on a silica-containing carrier and as promoters zirconium and a noble metal of Group VIII of the Periodic Table.

DESCRIPTION OF THE PREFERRED EMBODIMENTS

A preferred catalyst comprises cobalt together with zirconium and platinum or palladium as promoters, platinum being in particular preferred. Mixtures of two or more noble metal promoters may also be used, if desired. The amounts of cobalt and promoters prevailing in the catalyst may vary, but conveniently the catalyst preparation is performed in such a manner that the ultimate catalyst contains from 5-40 pbw cobalt, 0.25-50 pbw and in particular 0.5-25 pbw of zirconium and 0.0001-5 pbw, in particular 0.001-1 pbw of noble metal promoters per 100 pbw of silica containing carrier.

The carrier material in the catalysts according to the invention preferably consists of silica per se, although carrier material containing, in addition to $SiO_2$, minor amounts of other materials such as alumina or alumina silicates may be used as well.

The invention further relates to a method for the preparation of a cobalt, zirconium and noble metal-containing catalyst as hereinbefore defined. A preferred preparation method comprises the contacting of a porous silica-containing carrier with a cobalt compound and with compounds of the promoters to be incorporated, in the presence of a liquid, e.g. water, followed by the removal of the liquid, e.g. by evaporation, calcination of the composition at elevated temperatures and subsequent reduction in the presence of hydrogen. The impregnation of the various metals in the carrier may proceed in successive steps or in a single treatment. Suitable calcination temperatures are in the range of 400°-600° C., preferably between 450° and 500° C.

An advantage of the process according to the invention consists in that the reduction may be performed at a temperature which is substantially lower than that required in the reduction of catalysts that do not contain a promoter of a noble metal of Group VIII. In addition the reduction period adequate for the preparation of the catalysts according to the invention is significantly shorter than the period required in reducing calcined catalysts of the type known in the art.

Suitable reduction temperatures are in the range of 50°-300° C. The reduction period may be between 30 minutes and 24 hours whereby it will be clear that if a relatively low temperature is selected, a relatively long reduction period will be required and vice versa.

The invention further relates to a process for the preparation of hydrocarbons by contacting a mixture of carbon monoxide and hydrogen with a cobalt, zirconium and noble metal-containing catalyst, as hereinbefore defined.

The feed for this process may have been obtained, for instance, from a heavy carbon-containing material such as coal by gasification, or from light hydrocarbons, such as natural gas by steam reforming or partial oxidation.

Preferred reaction conditions are temperatures in the range of ±125°-350° C., in particular in the range of 175°-275° C. and pressures in the range of from 0.5 to 15 MPa, in particular in the range of from 1 to 10 MPa.

A preferred embodiment of the process according to the invention consists in that the preparation of hydrocarbons from carbon monoxide and hydrogen is used as the first step in a two-step process for the preparation of middle distillates.

To this end the hydrocarbon product, or at least that part of the product which has an initial boiling point above the final boiling point of the desired middle distillate fraction, is subjected to a catalytic hydrotreatment as the second step in the process.

The catalytic hydrotreatment is suitably carried out by contacting the hydrocarbon material from the first step at elevated temperatures and pressures and in the presence of hydrogen with a catalyst comprising one or more metals having hydrogenation activity, supported on a carrier.

In the hydrotreatment preference is given to the use of a catalyst comprising one or more metals from Group VIII, supported on a carrier. In particular, a catalyst is preferred comprising platinum on a carrier 13–15%w of which contains of alumina and the rest of silica. The preferred reaction conditions in the hydrotreatment are temperatures in the range of 175°–400° C., in particular in the range of 250°–350° C., a hydrogen partial pressure of 1 to 25 MPa, in particular of 2.5 to 15 MPa, a space velocity of 0.1–5 $kg.l^{-1}.h^{-1}$, in particular of 0.25–2 $kg.l^{-1}.h^{-1}$ and a hydrogen/oil ratio of 100–5000 $Nl.kg^{-1}$, in particular of 250–2500 $Nl.kg^{-1}$.

The invention is further illustrated with the following Example which is intended for illustration and not to be construed as limiting the invention.

EXAMPLE

Catalyst preparation.

Catalyst 1

A spherical silica carrier with an internal surface area of 112 m$^2$/ml (bulk volume) and an external surface area of 15 cm$^2$/ml (bulk volume) was dried at 120° C. The carrier was immersed during 15 sec in a solution of cobalt nitrate in ethanol and subsequently dried and calcined at 500° C. The treatment comprising of immersion, drying and calcination was repeated.

Subsequently the cobalt-loaded carrier was contacted with a solution of zirconium nitrate in water (pore volume impregnation). The carrier now loaded with cobalt and zirconium was calcined at 500° C.

The composition of the catalyst was 10 Co/0.9 Zr/100 SiO$_2$, its internal surface area was 94 m$^2$/ml (bulk volume).

Catalyst 2

A portion of catalyst 1 was loaded with platinum by pore volume impregnation with an aqueous solution of Pt(NH$_3$)$_4$(OH)$_2$, followed by drying at 120° C. and calcining at 500° C.

The composition of the catalyst was 0.1 Pt/10 Co/0.9 Zr/100 SiO$_2$, its internal and external surface area were identical with those of catalyst 1.

Catalyst testing

Catalysts 1 and 2 were tested for the conversion of synthesis gas in a tubular reactor in which the catalyst was present in the form of a fixed bed with a bulk volume of 10 ml.

Prior to the testing, the catalysts were reduced under the conditions as specified in the Table.

The conditions prevailing during the conversion of synthesis gas were:
Pressure: 2 MPa
Ratio H$_2$/CO: 2 (v/v)
GHSV (H$_2$+CO): 900 $Nl.l^{-1}.h^{-1}$ Further conditions and conversion results are given in the Table.

TABLE

| Catalyst | 1 | 2 |
|---|---|---|
| Reduction temperature, °C., | 260 | 115 →260 |
| Reduction time, h | 92 | 6 (during the first 5 h the temperature was in-increased from 115-260° C.) |
| Reduction pressure, MPa | 0.2 | 0.2 |
| Composition reduction gas | $\frac{H_2}{N_2} = \frac{1}{9}$ | $\frac{H_2}{N_2} = \frac{1}{9}$ |
| Conversion temperature, °C. | 210   220 | 210   220 |
| Conversion (h$_2$ + CO), % v | 32    57 | 51    69 |
| Space-time yield $g\, C_{1+}\cdot l^{-1}\cdot h^{-1}$ | 53    99 | 88    122 |
| Deactivation rate, Conversion loss per 100 h in % v abs |      2 |     <1 |
| C$_3$ selectivity, % w on C$_{1+}$ | 84    81 | 82    80 |

As can be seen from these results, catalyst 2 was by far superior as regards space-time yield and synthesis gas conversion, and a lower rate of deactivation.

We claim:

1. A process for the preparation of a catalyst useful for the preparation of hydrocarbons, the majority of which have more than three carbon atoms, from carbon monoxide and hydrogen which comprises contacting a porous silica-containing carrier with metal compounds comprising a cobalt compound, a zirconium compound and a noble metal compound selected from Group VIII of the Periodic Table and mixtures thereof dissolved in a liquid selected from the group consisting of water and ethanol, followed by the removal of the liquid, calcination of the resulting composition at elevated temperature and reduction in the presence of hydrogen at temperature in the range of from about 50° C. to about 300° C. for a period of time in the range of from about 30 minutes to about 24 hours; wherein the amount of cobalt in the catalyst is from about 5 to about 40 pbw per 100 pbw of silica-containing carrier, the amount of zirconium in the catalyst is from about 0.25 to about 50 pbw and the amount of the noble metal compounds in the catalyst is from about 0.0001 to about 5 pbw, on the same basis.

2. The process as claimed in claim 1, wherein the noble metal compound selected from Group VIII of the Periodic Table is a platinum compound.

3. The process as claimed in claim 1, wherein the reduction temperature is increased during the first 30 minutes to 10 hours from an initial temperature in the range of from about 50° C. to about 200° C. gradually to a temperature in the range of from about 210° C. to about 290° C. and held at the temperature in the range of from about 210° C. to about 290° C. for a period of time in the range of from about 30 minutes to about 2 hours.

4. The process as claimed in claim 1, wherein the reduction temperature is increased gradually from about 115° C. to about 260° C. during the first 5 hours and then held at about 260° C. for about an hour.

5. A process for the preparation of a catalyst useful for the preparation of hydrocarbons, the majority of which have more than three carbon atoms, from carbon monoxide and hydrogen comprising the steps of contacting a porous silica-containing carrier with metal compounds comprising a cobalt compound, a zirconium compound and a platinum compound dissolved in a liquid selected from the group consisting of water and ethanol, followed by the removal of the liquid, calcination of the resulting composition at elevated temperature and reduction in the presence of hydrogen; wherein the amount of cobalt is in the range of from about 5 pbw to about 40 pbw per 100 pbw of silica-containing carrier, the amount of zirconium is in the range of from about 0.5 pbw to about 25 pbw and the amount of platinum is in the range of from about 0.001 pbw to about 1 pbw per 100 pbw of silica-containing carrier; wherein the reduction temperature is increased from about 115° C. gradually to about 260° C. during the first five hours and then held at about 260° C. for about an hour.

6. A catalyst for the preparation of hydrocarbons, the majority of which have more than three carbon atoms, from hydrogen and carbon monoxide which is prepared by a process as claimed in claim 1.

7. The catalyst as claimed in claim 6, wherein said noble metal compound is a platinum compound.

8. The catalyst as claimed in claim 6, wherein the amount of cobalt is from about 5 to about 40 pbw per 100 pbw of silica-containing carrier, the amount of zirconium is from about 0.25 to about 50 pbw and the noble metal compound(s) is from about 0.001 to about 5 pbw, on the same basis.

9. The catalyst as claimed in claim 7, prepared by the process wherein the catalyst is reduced at a temperature which is increased during the first 30 minutes to 10 hours from an initial temperature in the range of from about 50° C. to about 200° C. gradually to a temperature in the range of from about 210° C. to about 290° C. and held at the temperature in the range of from about 210° C. to about 290° C. for a period of time in the range of from about 30 minutes to about 2 hours.

10. The catalyst as claimed in claim 7, prepared by the process wherein the reduction temperature is increased from about 115° C. to about 260° C. during the first 5 hours and then held at about 260° C. for about an hour.

* * * * *